United States Patent [19]

Leung et al.

[11] 4,238,389

[45] Dec. 9, 1980

[54] VALPROATE CONJUGATION USING DICARBONYLS

[75] Inventors: Danton K. Leung, San Jose; Prithipal Singh, Santa Clara, both of Calif.

[73] Assignee: Syva Company, Palo Alto, Calif.

[21] Appl. No.: 11,254

[22] Filed: Feb. 12, 1979

[51] Int. Cl.³ .................... C07C 103/52; A23J 1/00; C07G 7/00
[52] U.S. Cl. .................... 260/112.5 R; 260/112 R; 260/122
[58] Field of Search .................... 260/112.5 R, 112 R, 260/112.5, 122; 424/177, 322; 562/590

[56] References Cited

U.S. PATENT DOCUMENTS 3,325,361  6/1967  Merimer et al. .................... 424/322

OTHER PUBLICATIONS

Berthier, S. A., Chem. Abstract, vol. 74, 146380y (1971).

*Primary Examiner*—Delbert R. Phillips
*Assistant Examiner*—Blondel Hazel
*Attorney, Agent, or Firm*—Bertram I. Rowland

[57] ABSTRACT

α-substituted derivatives of valproic acid are provided for conjugation to antigenic compositions, particularly poly(amino acids), and enzymes. The antigenic conjugates are employed for the production of antibodies, which find particular use in immunoassays for the determination of valproate, while the enzyme conjugate finds use in a homogeneous enzyme immunoassay for the determination of valproate. The compounds are synthesized by alkylating valproate at the tertiary carbon atom by an aliphatic chain with a terminal double bond which is cleaved to provide an acid or aldehyde group.

15 Claims, No Drawings

VALPROATE CONJUGATION USING DICARBONYLS

BACKGROUND OF THE INVENTION

1. Field of the Invention

Valproate (sodium di-n-propylacetate) is recognized as an important antiepileptic drug. Its use as an anticonvulsant is beneficial due to its low toxicity. A minimum level of 50 μg/ml in serum is required for therapeutic efficacy; however, this level is often difficult to maintain due to individual differences in serum absorption and metabolism. It is therefore essential to monitor the serum levels regularly in order to insure that a minium therapeutic level of valproate is being maintained.

Of the current assay procedures for valproate, vapor phase chromatography analysis is the most widely used. Known techniques have various inadequacies in being uneconomical, slow and/or requiring trained clinicians to perform the assay properly. It is therefore desirable to provide a simple and rapid procedure for determining valproate levels in serum or other physiological fluids, which provides reproducible values and is specific for valproate.

The simple structure of vaproic acid—a saturated branched aliphatic acid—makes it one of the smallest and simplest drugs to be considered as a haptenprotein antigen for production of antibodies. As such, in the design of any hapten derivatives of valproic acid, to be used in the conjugation to proteins for the preparation of antigenic conjugates, there is little guidance as to the effect of structural modification on the specificity of antibodies.

2. Description of the Prior Art

Matsumoto et al., "Mass Spectrometry in Drug Metabolism" by Frigero and Ghesalberli, Plenum Publishing Corp., N.Y., N.Y. (1977) and Kuhara & Matsumoto, *Biomedical Mass Spectrometry*, 1, 291 (1974) teach that valproic acid is metabolized in humans via oxidation predominantly at the positions β and ω to the carboxylic acid, and is eventually excreted in urine as the free acids or via glucuronide formation. U.S. Pat. No. 3,817,837 describes a homogeneous enzyme immunoassay technique for the determination of a wide variety of drugs.

SUMMARY OF THE INVENTION

A synthetic procedure is provided for preparing novel α-substituted valproic acid derivatives and their conjugates to antigenic materials, in particular poly(amino acids) and enzymes. The antigenic conjugates are employed for the production of antibodies for use in immunoassays. The enzyme conjugates are employed as reagents for the determination of valproate in immunoassays. The antibodies and enzyme conjugates are provided in combination in kits to be used for the rapid and accurate determination of valproate in physiological fluids, e.g. serum.

DESCRIPTION OF THE SPECIFIC EMBODIMENTS

Compounds of the present invention are diacids, monoacid aldehydes, cyclic anhydrides and, as conjugates to poly(amino acids), amides formed from the cyclic anhydride or ester of derivatives of valproic acid or amines formed from the monoacid aldehyde derivatives of valproic acid.

Novel compounds are provided having at the α-position of valproic acid, a linking group having at least one spacer carbon atom and an active functionality for forming a covalent bond to antigens to provide conjugates for preparing antibodies to valproate and to enzymes for forming reagents for valproate determination. The linking group is normally an alkylene bonded to a carbonyl as the active functionality.

For the most part, the compounds of the invention will have the following formula:

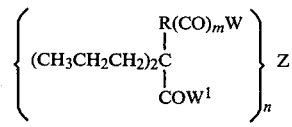

wherein:
- R is an aliphatic group, preferably alkylene, of from 1 to 6, usually 1 to 4 carbon atoms, and preferably 1 to 3 carbon atoms, having 0 to 1 site of aliphatic unsaturation, normally ethylenic. R is preferably saturated, and usually polymethylene;
- when m and n are both 1, W and $W^1$ may be taken together with Z to form a cyclic anhydride;
- otherwise when W and $W^1$ are not taken together, $W^1$ is hydroxyl;
- when m is 0, W is a methylene bonded to amino groups of Z and Z is a poly(amino acid) which is antigenic or an enzyme;
- when m is 1, W is a bond and Z is hydrogen, hydroxy, alkoxy of from 1 to 6 carbon atoms, preferably 1 to 3 carbon atoms, or an activating oxy group to form an activated ester capable of amide formation in an aqueous medium, e.g. N-oxy succinimide and p-nitrophenoxy; and
- n is 1 when Z is other than poly(amino acid) and is otherwise one to the molecular weight of Z divided by 500, more usually divided by 1000, and frequently divided by 1500, generally ranging from about 1 to 500, preferably from about 10 to 100, when Z is an antigen, and from 1 to 30, more usually 2 to 20, and preferably from about 2 to 16, when Z is an enzyme.

For those compounds where n is one, the compounds will have the following formula:

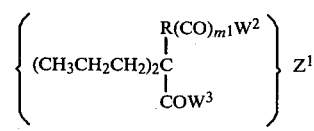

wherein:
- R is as defined previously, usually polymethylene of 1 to 3 carbon atoms when $Z^1$ is other than hydrogen and 2 to 6 carbon atoms when $Z^1$ is hydrogen;
- $m^1$ is 1;
- $W^2$ and $W^3$ may be taken together with $Z^1$ to form a cyclic anhydride;
- otherwise $W^2$ is a bond to $Z^1$ and $W^3$ is hydroxyl; and
- $Z^1$ is hydrogen, hydroxyl, alkoxy of from 1 to 6 carbon atoms, more usually from 1 to 3 carbon atoms, particularly methyl and ethyl, an oxy group forming an activated ester which readily reacts with the amine groups of poly(amino acids) under mild conditions in an aqueous medium, such as N-oxy succinimide or p-nitrophenyl.

When n is at least one and Z is a poly(amino acid), the compounds for the most part will have the formula:

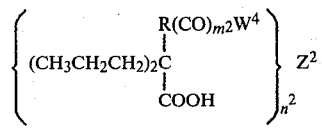

wherein:
R has been defined previously, usually polymethylene of from 1 to 3 carbon atoms when $W^4$ is a bond or of from 2 to 5 carbon atoms when $W^4$ is methylene;

$Z^2$ is a poly(amino acid) which is either antigenic or an enzyme;

$m^2$ is 0 or 1; when $m^2$ is 0, $W^4$ is methylene bonded to $Z^2$ through amino nitrogen, and when $m^2$ is 1, $W^4$ is a bond to $Z^2$ to form amide linkages;

$n^2$ is at least 1, usually greater than 1;

when $Z^2$ is an antigen, $n^2$ will normally be at least 2, and not greater than the molecular weight of $Z^2$ divided by 500, usually not greater than the molecular weight of $Z^2$ divided by 1000, and preferably not greater than the molecular weight of $Z^2$ divided by 1500, generally ranging from about 2 to 500; when $Z^2$ is an enzyme, $n^2$ will be at least 1, usually not greater than 30, more usually in the range of about 2 to 20, and preferably in the range of about 2 to 16.

The poly(amino acids) will generally range from about 5000 molecular weight, having no upper molecular weight limit, normally being not more that 10,000,000, usually not more than about 600,000. There will usually be different ranges, depending on whether an antigen or an enzyme is involved, with antigens ranging from about 5000 to $10^7$, usually from about 20,000 to 600,000, and more usually from about 25,000 to 250,000 molecular weight; while enzymes will generally range from about 10,000 to 600,000, more usually from about 10,000 to 300,000 molecular weight. There will usually be at least about one conjugate per 500,000 molecular weight, more usually at least one per 50,000 molecular weight. With intermediate molecular weight antigens (35,000 to 1,000,000), the number of conjugate groups will generally be from about 2 to 250, more usually from 10 to 100. With lower molecular weight antigens, below 35,000, the number of conjugates will generally be in the range of from about 2 to 10, usually in the range of 2 to 5.

Various protein types may be employed as the antigenic material. These types include albumins, serum proteins, e.g., globulins, ocular lens proteins, lipoproteins, etc. Illustrative proteins include bovine serum albumin, keyhole limpet hemocyanin, egg ovalbumin, bovine γ-globulin, etc. Alternatively, synthetic poly(amino acids) may be prepared having a sufficient number of available amino groups, e.g., lysines.

The enzymes can be varied widely, depending upon the rapidity with which one desires a result and the physiological fluid in which the valproate is to be measured. Primarily, the enzymes of choice, based on the I.U.B. classification are Class 1. Oxidoreductases and Class 3. Hydrolases. Particularly in Class 1, the enzymes of interest are dehydrogenases of Class 1.1, more particularly 1.1.1 and 1.1.99 and peroxidases, in Class 1.11. Of the hydrolases, particularly Class 3.1, more particularly 3.1.3 and Class 3.2, more particularly 3.2.1.

Illustrative dehydrogenases include malate dehydrogenase, glucose-6-phosphate dehydrogenase, and lactate dehydrogenase. Of the peroxidases, horse radish peroxidase is illustrative. Of the hydrolases, alkaline, phosphatase, β-galactosidase, β-glucosidase and lysozyme are illustrative.

Particularly preferred are those enzymes which employ nicotinamide adenine dinucleotide (NAD) or its phosphate (NADP) as a cofactor, particularly the former. Most perferred as the choice of enzyme is glucose-6-phosphate dehydrogenase.

In preparing the subject intermediates, the central (α) carbon atom in valproic acid furnishes one replaceable hydrogen for a site of alkylation. Carbanion format via the lithium salt allows for substitution of that hydrogen atom by an aliphatic chain with a terminal double bond, said double bond allowing for further conversion into an aldehyde or an acid group.

The synthetic scheme for preparing the subject compounds is set forth in the following chart:

CHART 1

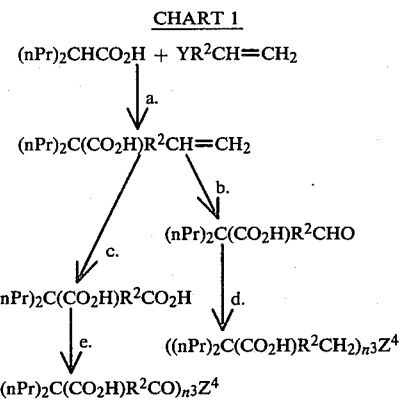

Y- halogen of atomic number 17–35
$Z^4H_{n3}$ - poly(amino acid)
$R^2$ - alkylene of 1 to 6 carbon atoms
$n^3$ - 1 to the molecular weight of $Z^4H_{n3}$ divided by 500
a. nBuLi and NaH
b. $O_3$, Zn
c. $MnO_4^\ominus$
d. $Z^4H_{n3}$ NaCNBH$_3$
e. where $R^2$ is alkylene of 1 to 3 carbon atoms,
   (1) Ac$_2$O, Δ
   (2) $Z^4H_{n3}$ The antigenic conjugates may be injected into a wide variety of vertebrates in accordance with conventional methods for the production of antibodies. Usually, the animals are bled periodically with the successive bleeds improving in titer and specificity and then plateauing and diminishing in their specificity and titer.

As previously indicated, the antibodies and enzyme reagents prepared in accordance with the subject invention find particular use in immunoassays for the determination of valproate. A description of the method for carrying out the immunoassay, which is a homogeneous enzyme immunoassay, may be found in U.S. Pat. No. 3,817,837. The method involves combining the enzyme conjugate, the unknown sample suspected of containing valproate, an antibody for valproate in an aqueous buffered medium at temperatures in the range of about 10° to 50°, more usually from about 20° to 40° C., and determining the enzyme activity as compared to the enzyme activity of an assay medium having a known amount of valproate.

EXPERIMENTAL

The following examples are offered by way of illustration and not by way of limitation.

(All temperatures not otherwise indicated are Centigrade. All percents not otherwise indicated are by weight. Parts are by weight, except when two liquids are combined and are then by volume. The following abbreviations are employed: HOAc—acetic acid; DMF—dimethylformamide; THF—tetrahydrofuran.)

EXAMPLE 1A

Preparation of 7-Carboxy-7-propyl-1-decene by the Alkylation of Valproic Acid with 6-Bromo-1-hexene Under an argon blanket, sodium hydride (1 g, 50% oil, 0.022 mole) was washed twice with hexane and the washings decanted. To the washed NaH was added 50 ml of THF (freshly distilled from LiAlH$_4$) and followed by the dropwise addition of valproic acid (2.88 g, 0.02 mole) in 20 ml of THF. The rate of addition was adjusted according to the amount of hydrogen evolved. The sodium salt was cooled in a salt ice bath to 0° and then diisopropylamine (2 g, 0.02 mole, distilled over CaH$_2$) was added. The mixture was heated to 55° for 15 minutes, and then cooled to room temperature in two hours. The solution was then cooled to −1° and n-butyllithium (10 ml, 0.02 mole) was added while keeping the temperature between about 0°–5°. After 15 minutes, the reaction mixture was warmed to 35° for 33 minutes and again cooled to 0°. To the cold reaction mixture was added dropwise cold (0°–2°) 6-bromo-1-hexene (3.2 g, 0.02 mole) in 20 ml of THF. The resulting solution was cooled in an ice bath for 30 minutes, then maintained at 33° for an hour. NaBr precipitated and the reaction mixture was allowed to stir overnight at room temperature. A sample of the solution was taken and shaken with D$_2$O; nmr showed no tertiary hydrogen present. The reaction mixture was then cooled in an ice bath, 25 ml of water was added and the mixture was extracted with 50 ml of ether. The ethereal solution had 50 ml of 5% K$_2$CO$_3$ added to it and then was extracted with 2×50 ml of hexane. The basic aqueous solution in an ice bath was acidified with concentrated HCl to pH 1, saturated with salt, and then extracted with 2×50 ml of ether. The ethereal solution was washed with 3×10 ml of brine, dried (MgSO$_4$) and concentrated to give 2.9 g of an oil. Tlc on silica (10% methanol in chloroform) gave a Rf 0.76 visualized by bromocresol green stain.

EXAMPLE 1B

Preparation of 6-Carboxy-6-propylnonanoic Acid

The 7-carboxy-7-propyl-1- decene (3.42 g, 0.015 mole) prepared in Example 1A was dissolved in 75 ml of acetone, 2 g of NaHCO$_3$ added and was cooled in an ice bath. Potassium permanganate (9.5 g, 0.06 mole) was added over four hours. The mixture was left in the cold bath for an additional hour and then NaHSO$_3$(8 g) was added alternately with 5 N H$_2$SO$_4$ to bring the pH to 2 and to reduce the residual permanganate. After filtering, the filtrate was concentrated to an oily residue which was extracted with 100 ml ethyl acetate, washed by water and saturated brine, dried (MgSO$_4$), concentrated to give an oil weighing 3.2 g and finally distilled by molecular distillation to give the pure product.

EXAMPLE 2

Preparation of the Conjugates of 6-Carboxy-6-propylnonanal with BgG and BSA

2A. Ozonolysis of 7-Carboxy-7-propyl-1-decene

The unsaturated acid (Ex.1A.) was dissolved in 25 ml of CH$_2$Cl$_2$ under an argon blanket and cooled to −45° with a dry-ice acetone bath. Ozone was introduced until a blue color persisted for 10 minutes. The reaction mixture was flushed with argon until colorless. Acetic acid (100 ml) and 50 ml of ether with 10 g of zinc dust were added and the mixture left at room temperature overnight. After filtering the filtrate was concentrated on a rotary evaporator to give 4.75 g of aldehyde (6-Carboxy-6-propylnonanal). Tlc on silica gel (50% EtOAc/benzene) gave Rf 0.63 (one spot stained by both ceric sulfate and 2,4-DNP). A derivature of 2,4-DNP-hydrazone was prepared, mp. 146°–148°.

2B. Preparation of 6-Carboxy-6-propylnonanal-BSA Conjugate

To 900 mg of BSA in 50 ml of phosphate buffer at pH 7.2 was added sodium cyanoborohydride (mixed with tritiated NaCNBH$_3$) and the 6-carboxy-6-propylnonanal prepared in Example 2A in 10 ml of carbitol. The solution was mixed at room temperature and stirred at 4° over the weekend. The conjugate solution was dialyzed with 7×4 liter of water adjusted to pH 9 with NH$_4$OH. Lyophilization gave 790 mg of conjugate. Hapten number was estimated to be 17 by tritium label.

2C. Preparation of 6-Carboxy-6-propylnonanal-BgG Conjugate

BgG (900 mg) and the 6-carboxy-6-propylnonanal (205 mg) prepared in Example 2A were employed for conjugation as described in Example 2B. Lyophilization yielded 550 mg of conjugate with a hapten number of 26.

EXAMPLE 3

Preparation of 2-Propyl-2-butenylpentanoic Acid

Into a dry 500 ml three-necked flask under argon was placed 4 g of NaH (50% oil, 0.087 mole). The NaH was washed twice with 50 ml hexane which was decanted and the clean NaH was flushed dry by argon. Freshly distilled THF (50 ml) was added and cooled to 0°–5°. Valproic acid (2-propylpentanoic acid, 11.52 g, 0.08 mole) in 50 ml THF was added dropwise to the NaH slurry over thirty minutes, followed by diisopropylamide (8 ml). The mixture was warmed to 55° for 15 minutes and allowed to cool to room temperature in two hours, then cooled to 2° in an ice bath. n-Butyllithium (40 ml, 2 M in hexane) was added via syringe at a temperature between 5°–10°. The resulting mixture was warmed to 35° for 30 minutes and then cooled to 2°. 4-Bromo-1-butene was added dropwise maintaining the pot temperature between 10°–20°. The reaction mixture was warmed again to 35° for 38 minutes and stirred at room temperature overnight. The reaction mixture was concentrated and added to 100 ml water, acidified to ph 1 with concentrated HCl and then extracted with 150 ml each of ether and ethyl acetate. The organic extract was washed with 4×50 ml water and 2×20 ml saturated brine, dried (magnesium sulfate), and concentrated to give a yellow liquid weighing 15 g. Distillation gave 10 g of a colorless liquid, bp. 90°/0.05 mm Hg. Tlc on silica (1:1 ether: hexane) gave Rf 0.63, stained by bromocresol green.

EXAMPLE 4.

Preparation of 2-Propyl-2-(2'-carboxyethyl)-pentanoic Acid and 2-Propyl-2-(carboxymethyl)-pentanoic Acid 2-Propyl-2-butenylpentanoic acid (3 g, 0.015 mole) prepared in Example 3 was dissolved in 100 ml of acetone and $NaHCO_3$ (1 g, 0.018 mole) was added. The mixture was cooled in an ice bath, and then potassium permanganate (9.5 g, 0.06 mole) was added over 5 hours and the mixture stirred for an additional hour at room temperature. After being cooled in an ice bath the mixture was acidifed to pH 2 with 5 N $H_2SO_4$ and then $NaHSO_3$ (9 g, 0.096 mole) was added until the purple color of the permanganate disappeared. The mixture of colorless aqueous solution and brown manganese dioxide was filtered through Celite. The filtrate was concentrated to a small aqueous volume and extracted with 150 ml each of ether and ethyl acetate, washed with brine, dried ($MgSO_4$), and concentrated to give a slightly colored liquid weighing 3 g. Tlc on silica with 10% methanol in chloroform gave Rf 0.45.

The relative proportions of 2-propyl-2-(-2'-carboxyethyl)pentanoic acid and 2-propyl-2-carboxymethylpentanoic acid were dependent on the control of the reaction time and temperature, the former being present in an amount equal to about 70-90%.

EXAMPLE 5

Cyclization of 2-Propyl-2-(2'-carboxyethyl)-pentanoic Acid and 2-Propyl-2-carboxymethylpentanoic Acid To a mixture of the two diacids (3 g) as prepared in Example 4 was added 10 ml of distilled acetic anhydride under argon. The solution was then heated to 120° in two hours, kept at 120° for an additional 2 hours and then heated to 130°. The solution was concentrated to dryness to give a crude product of 3 g. Gas chromatography on S.E. 30 column at 185° separated the two cyclic anhydrides, 2,2-dipropylglutaric anhydride and 2,2-dipropylsuccinic anhydride, in pure form.

EXAMPLE 6

Conjugation of 2-Propyl-2-(2'-carboxyethyl)-pentanoic Acid to BSA (Bovine Serum Albumin)

To a solution of BSA (300 mg, $5 \times 10^{-4}$ mmole) in 20 ml of phosphate buffer was added the hapten, 2,2-dipropylglutaric anhydride as prepared in Example 5 (55 mg, 0.25 mmole in 200 ml THF) in 4μl portions over an hour. The resulting clear solution was stirred at 4° overnight, after which it was dialyzed in 7×2 liter of water adjusted to pH 8 with phosphate buffer, followed by one time with deionized water. The dialysis took 5 days. Lyophilization gave 320 mg of conjugate having a hapten number of 40 as estimated by the amino group precipitation method.

EXAMPLE 7.

Conjugation of 2-Propyl-2-(2'-carboxyethyl)-pentanoic Acid to Glucose-6-phosphate Dehydrogenase (G6PDH)

The 2,2-dipropylglutaric anhydride prepared in Example 5 (4.0 mg) was solubilized in 100μl of DMF and then added to a stirring solution of 2 ml of G6PDH (Beckman Lot HO1, 4.3 mg/ml), 40 mg of G6P disodium salt and 60 mg of NADH. Carbitol (600μl) was then slowly added, the solution having a final pH of about 8.7-8.9. The pH was maintained during the reaction by addition of NaOH.

The enzyme was monitored in accordance with the enzyme assay to be described for determining % deactivation. The % inhibition was determined by adding an excess of anti(valproate) and assaying the enzyme activity according to the method described.

Table 1 shows the progress of the conjugation.

TABLE 1

| Sample No. | Total Hapten(μl) | % Deactivation | % Inhibition |
|---|---|---|---|
| 1 | — | | |
| 2 | — | | |
| 3 | 8 | 8 | 15 |
| 4 | 16 | 18 | 30 |
| 5 | 26 | 27 | 45 |
| 6 | 36 | 35 | 58 |
| 7 | 36 | 36 | 60.5 |
| 8 | 41 | 39 | 64 |
| 9 | 49 | 45 | 70 |

The conjugate was worked up by chromatography over Sephadex G-50 M (180 ml column), employing 0.055 M tris-HCl buffer (pH 8.1) as eluent, collecting 2.6 ml samples (~1.5% sample/bed volume ratio). Fractions were pooled to give a total volume of 20.5 ml.

In order to demonstrate the efficacy of compounds prepared in accordance with the subject invention, antibodies prepared from the conjugates described previously and the enzyme conjugate were employed in a number of assays for valproate. In carrying out the assay, a Gilford 300 N microsample spectrophotometer is employed with a Thermocuvette with a flow cell. All readings are made at 340 mn. The following solutions are prepared as reagents for use in the assay.

| Buffer: | 0.055M tris-HCl pH8.1 (RT) |
|---|---|
| Enzyme Conjugate: | Buffer |
| | 0.9% NaCl |
| | 1.0% RSA, pH8.1 (RT) |
| | Sufficient enzyme conjugate to give a maximum rate of ΔOD equal to 600-900 in the assay medium |
| Assay buffer: | Buffer |
| | 0.5% NaCl |
| | 0.01% v/v Triton X-100, pH8.1(RT) |
| Antibody Reagent: | Buffer |
| | 1.0% RSA, |
| | G6P(Na) 0.066M, |
| | NAD 0.04M, pH5 (RT) |
| | Antivalproate optimized for assay |
| | (All % indicated are w/v g/ml. RSA-rabbit serum albumin). |

The protocol employed for carrying out an assay is as follows: A sample, 50μl is drawn up into a diluter and dispensed with 250μof the assay buffer into a one ml Croan cup. A 50μl aliquot of the diluted sample is drawn up and dispensed with a 250μl portion of assay buffer into a second Croan cup. Into the second Croan cup is introduced 50μl of the antibody reagent with 250μl of the assay buffer, followed by the addition of 50μl of the enzyme reagent and 250μl of the assay buffer. Immediately after the enzyme addition, the entire sample is aspirated into the flow cell. After 10 seconds, a first reading is taken, followed by a second reading, after a 40 second interval from aspiration. The results are reported as the difference in absorbance ×2.667.

| Sample Concentration of Valproate μg/ml | ΔOD |
|---|---|
| 0 | (581)* — |
| 25 | 630 |
| 50 | 646 |
| 75 | 666 |
| 100 | 682 |
| 150 | 714 |
| max rate (1010)** | |

*lowest rate in assay with predetermined amount of antibody
**rate of enzyme in absence of antibody It is evident from the above results, that the compositions of the present invention provide, for reagents which can be used in a sensitive immunoassay for valproic acid. Thus a rapid accurate method is provided for the determination of valproic acid, which can be used in therapeutic dosage monitoring of patients to ensure that a therapeutic dosage is applied.

The antigenic conjugates of the subject invention provide for the production of highly specific antibodies. This result is obtained despite the fact that the tertiary carbon atom of valproate, adjacent the only polar group in the molecule is changed to a quaternary carbon atom, so as to enhance steric crowding at this site and to increase the hydrophobicity about the carboxyl group. In addition, the enzyme conjugates are able to complete with valproate for antibodies to provide a sensitive accurate assay.

Although the foregoing invention has been described in some detail by way of illustration and example for purposes of clarity and understanding, it will be obvious that certain changes and modifications may be practiced within the scope of the appended claims.

What is claimed is:

1. A conjugate of a compound selected from the group consisting of: 2-propyl-2-carboxymethylpentanoic acid, 2-propyl-2-(2'-carboxyethyl)pentanoic acid, 2,2-dipropylglutaric anhydride, 2,2-dipropylsuccinic anhydride, 6-carboxy-6-propylnonanal, and 2-carboxy-2-propylnonanoic acid, with a poly(amino acid) antigen or an enzyme.

2. A conjugate according to claim 1 wherein said conjugate has an enzyme which is glucose-6-phosphate dehydrogenase.

3. Conjugate according to claim 1 having a poly(amino acid) antigen.

4. Compound of the formula:

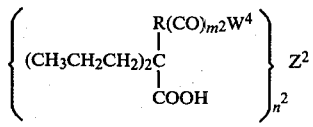

wherein:
R is an aliphatic group of from 1 to 6 carbon atoms;
$W^1$ is hydroxyl;
when m is 0, W is a methylene bonded to Z through amino nitrogen, and Z is a poly(amino acid);
when m is 1, W is a bond to Z, and Z is poly(amino acid) wherein W is bonded to said poly(amino acid) to amino groups to form amide linkages; and
n is one to the molecular weight of Z divided by 500.

5. Compound according to claim 4, wherein R is from 1 to 4 carbon atoms.

6. Compound according to claim 5, wherein Z is an enzyme and n is of from 1 to 30.

7. Compound according to claim 5, wherein Z is an antigen and n is in the range of from about 1 to 500.

8. Compound of the formula:

$$\left\{ \begin{array}{c} R(CO)_{m2}W^4 \\ | \\ (CH_3CH_2CH_2)_2C \\ | \\ COOH \end{array} \right\}_{n^2} Z^2$$

wherein:
R is an alkylene group of from 1 to 6 carbon atoms;
$m^2$ is 0 or 1;
$Z^2$ is a poly(amino acid);
$n^2$ is at least 1 and not greater than the molecular weight of $Z^2$ divided by 500; and
when $m^2$ is 0, $W^4$ is methylene bonded to amino groups of $Z^2$ and when $m^2$ is 1, $W^4$ is a bond to amino groups of $Z^2$ to form amide linkages.

9. Compound according to claim 8, wherein $Z^2$ is an enzyme and $n^2$ is in the range of 2 to 16.

10. Compound according to claim 9, wherein said enzyme is glucose-6-phosphate dehydrogenase.

11. Compound according to claim 8, wherein $Z^2$ is an antigen, and $n^2$ is in the range of about 2 to 500.

12. Compound according to claim 11, wherein said antigen is a globulin.

13. Compound according to claim 11, wherein said antigen is an albumin.

14. Conjugate according to claim 3, wherein said antigen is globulin.

15. Conjugate according to claim 3, wherein said antigen is albumin.

* * * * *